US007700056B2

(12) United States Patent
Hill et al.

(10) Patent No.: US 7,700,056 B2
(45) Date of Patent: Apr. 20, 2010

(54) MODULAR DECONTAMINATION SYSTEM

(75) Inventors: Aaron L. Hill, Erie, PA (US); Leslie M. Logue, Edinboro, PA (US); Ryan A. Bruskevith, Erie, PA (US)

(73) Assignee: American Sterilizer Company, Mentor, OH (US)

( * ) Notice: Subject to any disclaimer, the term of this patent is extended or adjusted under 35 U.S.C. 154(b) by 422 days.

(21) Appl. No.: 11/463,608

(22) Filed: Aug. 10, 2006

(65) Prior Publication Data

US 2008/0038166 A1 Feb. 14, 2008

(51) Int. Cl.
*A61L 2/16* (2006.01)
(52) U.S. Cl. .............................. 422/292; 422/3; 422/28; 422/105; 422/108; 422/298
(58) Field of Classification Search .................. 422/292, 422/3, 28, 37, 105, 10, 298
See application file for complete search history.

(56) References Cited

U.S. PATENT DOCUMENTS

| | | | |
|---|---|---|---|
| 4,204,037 A | 5/1980 | Dill et al. ........................ 453/3 |
| 4,241,010 A | 12/1980 | Baran ............................. 422/2 |
| 4,591,485 A | 5/1986 | Olsen et al. ..................... 422/20 |
| 4,843,867 A | 7/1989 | Cummings ...................... 73/23 |
| 4,863,688 A | 9/1989 | Schmidt et al. ................ 422/28 |
| 4,908,188 A | 3/1990 | Jefferis et al. ................ 422/111 |
| 4,952,370 A | 8/1990 | Cummings et al. ............. 422/28 |
| 4,956,145 A | 9/1990 | Cummings et al. ............. 422/28 |
| 5,020,481 A | 6/1991 | Nelson ........................ 122/494 |
| 5,114,670 A | 5/1992 | Duffey ......................... 422/24 |
| 5,122,344 A | 6/1992 | Schmoegner ................ 422/111 |
| 5,173,258 A | 12/1992 | Childers ........................ 422/27 |
| 5,418,167 A | 5/1995 | Matner et al. ................ 435/288 |
| 5,492,672 A | 2/1996 | Childers et al. ............... 422/28 |
| 5,650,693 A | 7/1997 | Campbell et al. ...... 315/111.21 |
| 5,770,393 A | 6/1998 | Dalmasso et al. .............. 435/31 |
| 5,788,925 A | 8/1998 | Pai et al. ......................... 422/3 |
| 5,866,356 A | 2/1999 | Albert et al. ................... 435/31 |

(Continued)

FOREIGN PATENT DOCUMENTS

WO  WO 97/47331  12/1997
WO  WO 03/082355  10/2003

OTHER PUBLICATIONS

U.S. Appl. No. 11/421,265, filed May 31, 2006, Buczynski, entitled: Decontamination System With Air Bypass.

(Continued)

*Primary Examiner*—Sean E Conley
(74) *Attorney, Agent, or Firm*—Kusner & Jaffe; Michael A. Centanni (57) ABSTRACT

A decontamination system having modular components to efficiently decontaminate enclosures of various dimensions. The decontamination system includes a main unit comprising a controller, a supply of liquid decontaminant, a vaporizer for vaporizing the liquid decontaminant to generate a vaporized decontaminant, and a destroyer for breaking down hydrogen peroxide into water and oxygen. An embodiment of the present invention includes a detachable dryer and a detachable external blower that are in fluid communication with the main unit. An optional external destroyer and an optional external dryer may be controlled by the controller of the main unit to respectively increase the destroying and drying capacity of the decontamination system.

20 Claims, 4 Drawing Sheets

U.S. PATENT DOCUMENTS

| | | | |
|---|---|---|---|
| 5,872,359 A | 2/1999 | Stewart et al. | 250/339.12 |
| 5,876,664 A | 3/1999 | Childers et al. | 422/28 |
| 5,882,590 A | 3/1999 | Stewart et al. | 422/28 |
| 5,906,794 A | 5/1999 | Childers | 422/28 |
| 6,156,267 A | 12/2000 | Pai et al. | 422/3 |
| 6,369,112 B1 | 4/2002 | Xia | 514/635 |
| 6,379,615 B1 | 4/2002 | Ogle | 422/28 |
| 6,387,648 B1 | 5/2002 | Levi et al. | 435/26 |
| 6,428,746 B1 | 8/2002 | Muscarella et al. | 422/3 |
| 6,455,272 B1 | 9/2002 | Gillis | 435/31 |
| 6,513,378 B1 | 2/2003 | Love, Jr. | 73/313 |
| 6,528,016 B1 | 3/2003 | Kohler et al. | 422/28 |
| 6,718,077 B1 | 4/2004 | Ferreira et al. | 385/12 |
| 6,787,105 B2 | 9/2004 | Robbins | 422/22 |
| 6,803,728 B2 | 10/2004 | Balasubramaniam et al. | 315/149 |
| 6,953,549 B2 | 10/2005 | Hill et al. | 422/30 |
| 7,157,046 B2 | 1/2007 | McVey et al. | 422/28 |
| 7,186,374 B2 | 3/2007 | Zelina et al. | 422/28 |
| 7,238,330 B2 | 7/2007 | Hill et al. | 422/292 |
| 7,252,800 B2 | 8/2007 | Jacobs et al. | 422/33 |
| 2002/0114727 A1 | 8/2002 | McVey et al. | 422/4 |
| 2002/0159915 A1 | 10/2002 | Zelina et al. | 422/3 |
| 2003/0031589 A1 | 2/2003 | Martin et al. | 422/28 |
| 2003/0063997 A1 | 4/2003 | Fryer et al. | 422/3 |
| 2003/0138344 A1 | 7/2003 | Mielnik et al. | 422/2 |
| 2003/0164091 A1 | 9/2003 | Hill et al. | 95/90 |
| 2004/0076358 A1 | 4/2004 | Ferreira et al. | 385/12 |
| 2004/0105758 A1 | 6/2004 | Ross | 417/44.1 |
| 2004/0154965 A1 | 8/2004 | Baum et al. | 210/85 |
| 2005/0079096 A1 | 4/2005 | Brown-Skrobot et al. | 422/24 |
| 2005/0252274 A1 | 11/2005 | Centanni | 73/23.2 |
| 2005/0274656 A1 | 12/2005 | McKinney | 210/86 |
| 2005/0276723 A1 | 12/2005 | Sundaram et al. | 422/28 |
| 2006/0008379 A1 | 1/2006 | Mielnik et al. | 422/32 |
| 2006/0061953 A1 | 3/2006 | Le | 361/684 |
| 2006/0088441 A1 | 4/2006 | Hill | 422/30 |
| 2006/0099106 A1 | 5/2006 | Watling et al. | 422/3 |
| 2006/0257877 A1 | 11/2006 | Anderle et al. | 435/6 |
| 2007/0014691 A1 | 1/2007 | Lin et al. | 422/62 |
| 2007/0098592 A1 | 5/2007 | Buczynski et al. | 422/3 |
| 2008/0038166 A1 | 2/2008 | Hill et al. | 422/292 |
| 2008/0267818 A1 | 10/2008 | Hill | 422/28 |

OTHER PUBLICATIONS

U.S. Appl. No. 11/740,973, filed Apr. 27, 2007, Hill, entitled: Vaporized Hydrogen Peroxide Probe Calibration Rig.

U.S. Appl. No. 11/741,069, filed Apr. 27, 2007, Hill, entitled: Vaporized Hydrogen Peroxide Decontamination System With Concentration Adjustment Mode.

U.S. Appl. No. 11/741,299, filed Apr. 27, 2007, Hill, entitled: Hydrogen Peroxide Vaporizer.

U.S. Appl. No. 11/838,327, filed Aug. 14, 2007, Hill, entitled: Method and Apparatus for Decontaminating a Region Without Dehumidification.

"Steris VHP® 1000ED Mobile Biodecontamination System," Low Temperature Biodecontamination, Steris Corporation, Aug. 2005.

"Introducing the Steris VHP® 100 Biodecontamination Systems," Low Temperature Biodecontamination, Steris Corporation, 2002.

"MDS™—Series, Modular Dehumidification System," Munters Product Information, Munters Corporation, Feb. 1999.

"Modular Dehumidification Systems," Dehumidification Division, Munters Corporation, 2000.

MODULAR DECONTAMINATION SYSTEM

FIELD OF THE INVENTION

The present invention relates generally to the field of decontamination systems that use a decontaminant in a gaseous or vaporous phase, and more particularly to a decontamination system that is adaptable to efficiently decontaminate enclosures of various dimensions.

BACKGROUND OF THE INVENTION

Decontamination methods are used in a broad range of applications, and have used an equally broad range of decontaminating agents. As used herein the term "decontamination" refers to the inactivation of bio-contamination, and includes, but is not limited to, sterilization and disinfection.

One common method for decontaminating an enclosure (e.g., a room) is to blow air through the enclosure in a continuous loop, i.e., from the enclosure, through a vaporized hydrogen peroxide (VHP) unit, and back into the enclosure. A typical VHP unit includes a blower, a catalytic destroyer, a dryer, a vaporizer, a preheater and an injection pump. The blower circulates the air through the continuous loop at a regulated flow rate. The catalytic destroyer breaks down vaporized hydrogen peroxide withdrawn from the enclosure into water and oxygen. The dryer removes water vapor from the air circulating therethrough. The pre-heater heats the air to facilitate the vaporization process. The vaporizer includes a heated surface to vaporize liquid decontaminant that is injected into the vaporizer by the injection pump. The injection pump controls the amount of decontaminant that is vaporized per unit time.

A VHP decontamination cycle is commonly divided into (4) four phases, namely, a dehumidification phase, a conditioning phase, a decontamination phase and an aeration phase. In the dehumidification phase, the relative humidity within the enclosure is reduced by using the dryer. After the dehumidification phase is complete, the conditioning phase commences, wherein vaporized hydrogen peroxide is injected into the enclosure at a relatively high rate to bring the vaporized hydrogen peroxide concentration up to a desired level in a short period of time. After the conditioning phase, the decontamination phase is run where the injection rate may be modified to maintain the hydrogen peroxide vapor in the enclosure at a constant concentration level. In the aeration phase that follows the decontamination phase, the enclosure is aerated by ending injection of the hydrogen peroxide vapor, and removing hydrogen peroxide vapor from the enclosure. The destroyer is used to break down the hydrogen peroxide vapor into water and oxygen. Aeration continues until the concentration of vaporized hydrogen peroxide in the enclosure is below a threshold concentration level (e.g., 1 ppm).

Existing VHP decontamination systems have several drawbacks. In this regard, the components of existing VHP decontamination systems can be heavy, thus making the components difficult to transport to a desired location. Components of existing VHP decontamination systems also may not have adequate capacity or features to properly decontaminate enclosures of various dimensions (e.g., large rooms or emergency vehicle enclosures).

The present invention provides a modular decontamination system that addresses these and other drawbacks of existing decontamination systems.

SUMMARY OF THE INVENTION

In accordance with a preferred embodiment of the present invention, there is provided a vapor decontamination system for decontaminating a region, said system comprising: (a) a main unit including: a vaporizer for generating vaporized hydrogen peroxide from an aqueous solution of hydrogen peroxide, a reservoir for providing the aqueous solution of hydrogen peroxide, a first destroyer for breaking down said vaporized hydrogen peroxide, a first input port, first and second output ports, and a controller for controlling operation of the vapor decontamination system; and (b) a first dryer detachable from said main unit, said first dryer including: an inlet port fluidly connectable with said first output port, and an outlet port fluidly connectable with said first input port.

An advantage of the present invention is the provision of a VHP decontamination system that can be configured to include additional destroyer capacity to facilitate destruction of vaporized hydrogen peroxide into water and oxygen.

Another advantage of the present invention is the provision of a VHP decontamination system that can be configured to include additional dryer capacity to facilitate dehumidification.

Still another advantage of the present invention is the provision of a VHP decontamination system that includes a detachable dryer tank to facilitate dryer regeneration.

Still another advantage of the present invention is the provision of a VHP decontamination system that includes a detachable blower to facilitate dispersion of hydrogen peroxide vapor.

Still another advantage of the present invention is the provision of a VHP decontamination system that includes an external power switching means for controlling power to one or more external components.

Yet another advantage of the present invention is the provision of a VHP decontamination system that includes a controller having advanced control functions to provide improved decontamination cycle control.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawing which form a part hereof and wherein.

DETAILED DESCRIPTION OF THE INVENTION

Figure 1:
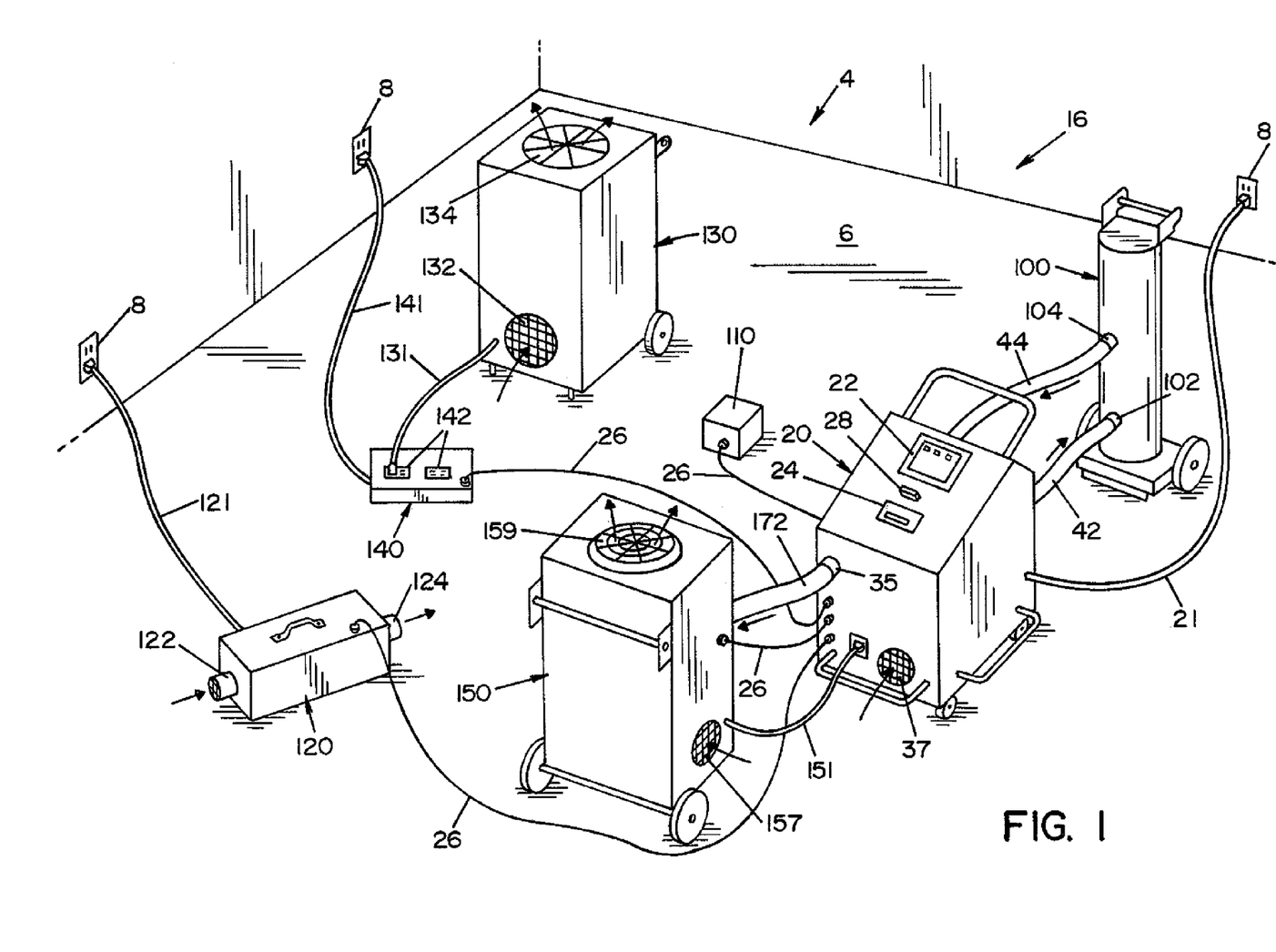
FIG. 1 is a perspective view of a modular vaporized hydrogen peroxide (VHP) decontamination system, according to one embodiment of the present invention.

Referring now to the drawings wherein the showings are for the purposes of illustrating a preferred embodiment of the invention only and not for the purposes of limiting same, FIG.

Figure 2:
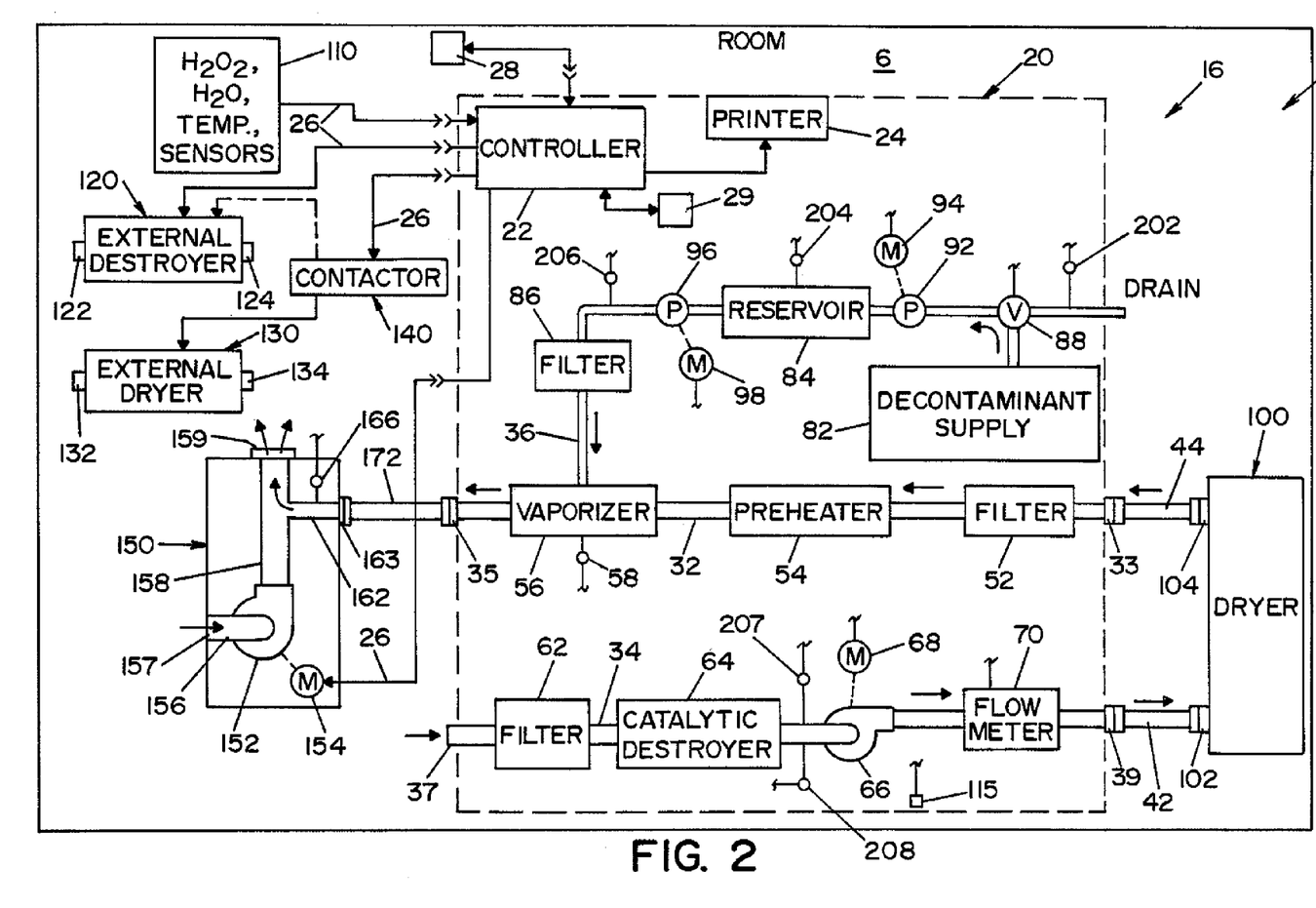
FIG. 2 is a schematic view of the modular VHP decontamination system shown in FIG. 1.

1 shows a perspective view of a modular vaporized hydrogen peroxide (VHP) decontamination system 16, according to a first embodiment of the present invention. System 16 is located within an enclosure, such as a room or a sealed vehicle enclosure (e.g., a patient compartment of an ambulance or an emergency rescue vehicle). In the embodiment shown in FIG. 1, system 16 is located within a room 4 that defines a chamber or region 6. Articles disposed within region 6 are decontaminated using system 16, as will be described in detail below. FIG. 2 provides a schematic view of system 16.

In the illustrated embodiment, modular VHP decontamination system 16 includes a VHP unit 20, a dryer 100, an external destroyer 120, an external dryer 130, a contactor unit 140 and an external blower unit 150.

VHP unit 20 will now be described in detail with particular reference to FIG. 2. VHP unit 20 is the main unit of decontamination system 16, and includes a supply conduit 32, a return conduit 34 and a feed conduit 36. Supply conduit 32 has an input port 33 and an output port 35. A filter 52, a preheater 54, and a vaporizer 56 are disposed in supply conduit 32. Vaporizer 56 includes a vaporization chamber (not shown), wherein a liquid decontaminant (i.e., an aqueous solution of hydrogen peroxide) is heated to form a gaseous or vaporized decontaminant (i.e., vaporized hydrogen peroxide) by conventionally known means. A temperature sensor 58 provides a signal indicative of the temperature in the vaporization chamber of vaporizer 56. Preheater 54, located upstream of vaporizer 56, heats a carrier gas (i.e., air) within supply conduit 32 to facilitate vaporization of the liquid decontaminant within vaporizer 56. Filter 52, also located upstream of vaporizer 56, filters the gas passing through supply conduit 32.

Feed conduit 36 provides a pathway for supplying the aqueous solution of hydrogen peroxide to vaporizer 56. A first end of feed conduit 36 is in fluid communication with vaporizer 56, while a second end of feed conduit 36 is fluidly connectable with a decontaminant supply 82 or a drain. In this regard, the second end of feed conduit 36 terminates at a first port of a three-way valve 88. A second port of three-way valve 88 is connected with a decontaminant supply 82, and a third port of three-way valve 88 is connected with the drain. Valve 88 is moveable between a first position and a second position. In the first position, valve 88 puts feed conduit 36 in fluid communication with decontaminant supply 82. In the second position, valve 88 puts feed conduit 36 in fluid communication with the drain.

Decontaminant supply 82 provides a supply of the aqueous solution of hydrogen peroxide. A typical aqueous solution of hydrogen peroxide is comprised of about 30% to 59% hydrogen peroxide by weight. It should be appreciated that the aqueous solution of hydrogen peroxide may have other concentrations of hydrogen peroxide. Decontaminant supply 82 may take the form of a replaceable cartridge.

A reservoir 84, a filter 86, a supply pump 92 and an injection pump 96 are disposed in feed conduit 36. Supply pump 92, driven by a motor 94, is operable to pump liquid decontaminant from decontaminant supply 82 to reservoir 84. Pump 92 may be activated when the level of liquid decontaminant in reservoir 84 has dropped below a predetermined level. A balance or pressure transducer may be used to provide a signal indicative of the mass or volume of liquid decontaminant stored in reservoir 84. It should be appreciated that since the density of the liquid decontaminant is known, the relationship between the measured pressure and the mass (or volume) of the liquid decontaminant in reservoir 84 can be determined.

Injection pump 96, driven by motor 98, is operable to inject a metered amount of liquid decontaminant from reservoir 84 to vaporizer 56 by conventionally known means. Injection pump 96 may include an encoder (not shown) that provides a signal indicative of pump revolutions, thereby allowing monitoring of the amount of liquid decontaminant being metered to vaporizer 56. Filter 86 filters the liquid decontaminant before it is received by vaporizer 56.

When valve 88 is in the first position, feed conduit 36 is in fluid communication with decontaminant supply 82, thereby allowing reservoir 84 to be filled with liquid decontaminant using supply pump 92. When valve 88 is in the second position, valve 88 puts feed conduit 36 in fluid communication with the drain, thereby allowing liquid decontaminant within reservoir 84 to be removed from VHP unit 20.

A first pressure sensor 202 is disposed between valve 88 and the drain to provide a signal indicative of the pressure of the fluid flowing to the drain. A second pressure sensor 204 provides a signal indicative of the level of liquid decontaminant within reservoir 84. A third pressure sensor 206 is disposed within feed conduit 36 downstream of reservoir 84 to provide a signal indicative of the pressure within feed conduit 36.

It has been observed that if VHP unit 20 leaks liquid decontaminant, the liquid decontaminant could eventually spill onto a surface below VHP unit 20 (e.g., a floor or carpet) thereby creating a hazard. Accordingly, VHP unit 20 may include an optional leak detector 115 located in a leak tight well or collection pan at the bottom of the housing for VHP unit 20. Leak detector 115 may take the form of a sensing device (e.g., a float switch or conductivity sensor) that provides a signal indicating the presence of liquid in the well or collection pan. The leak tight well or collection pan preferably has a capacity large enough to hold the volume of liquid decontaminant stored in reservoir 84.

Return conduit 34 has an input port 37 and an output port 39. A catalytic destroyer 64, a blower 66 and a flowmeter 70 are disposed in return conduit 34. Blower 66, driven by a motor 68, is operable to draw fluid through return conduit 34. Catalytic destroyer 64, located upstream of blower 66, is operable to destroy hydrogen peroxide flowing therethrough, by converting vaporized hydrogen peroxide into water and oxygen, as is conventionally known. A temperature sensor 208, located downstream of catalytic destroyer 64, provides a signal indicative of the temperature within return conduit 34. A humidity sensor 207 provides the relative humidity of the air within return conduit 34. The temperature and relative humidity are used to determine the absolute humidity (mass of water per volume of dry air). A flowmeter 70 is disposed in return conduit 34 downstream of blower 66. Flowmeter 70 provides a signal indicative of the fluid flow rate though return conduit 34. A filter 62, located upstream of catalytic destroyer 64, filters fluid entering return conduit 34 via input port 37. Filter 62 is preferably a high efficiency particulate air (HEPA) filter.

VHP unit 20 also includes a controller 22. Controller 22 includes a conventional microcontroller or microcomputer, display means (e.g., printer 24, and/or LCD/LED display unit), input means (e.g., a touch screen or panel), and a universal serial bus (USB) connection that allows connection with a USB memory device 28. USB memory device 28 may store data in an encrypted format. A flash memory device 29 (e.g., CompactFlash RAM Memory) may also be connected with controller 22. Controller 22 transmits control signals to vaporizer 56; motors 68, 94, 98; preheater 54; and valve 88. Controller 22 receives data signals from flowmeter 70; temperature sensors 58, 208; pressure sensors 202, 204, 206;

humidity sensor 207; and leak detector 115. Controller may also receive data signals from the balance or pressure transducer associated with reservoir 84, and the encoder associated with injection pump 96. As will be described in further detail below, controller 22 also communicates with components external to VHP unit 20, including external destroyer 120, contactor unit 140, external blower unit 150, and sensors of a sensor module 110. VHP unit 20 is connected to a power source via a power cord 21. In this regard, power cord 21 is connected to a room electrical outlet 8 (FIG. 1).

In the illustrated embodiment, dryer 100 is detachable from VHP unit 20, and preferably takes the form of a conventionally known regenerative desiccant dryer that collects water vapor from a fluid stream passing therethrough. Regenerative desiccant dryers use a desiccant (e.g., silica gel, activated alumina and molecular sieve), which sorbs water vapor in the fluid stream. In the embodiment shown, dryer 100 is a separate module that includes an inlet port 102 and an outlet port 104 to fluidly connect dryer 100 with VHP unit 20. In this regard, inlet port 102 of dryer 100 is fluidly connected with output port 39 of return conduit 34, via a dryer inlet conduit 42. Similarly, outlet port 104 of dryer 100 is fluidly connected with input port 33 of supply conduit 32, via a dryer outlet conduit 44. Accordingly, fluid entering return conduit 34 through input port 37, flows through dryer 100, and then returns to VHP unit 20 via supply conduit 32.

Figure 4:
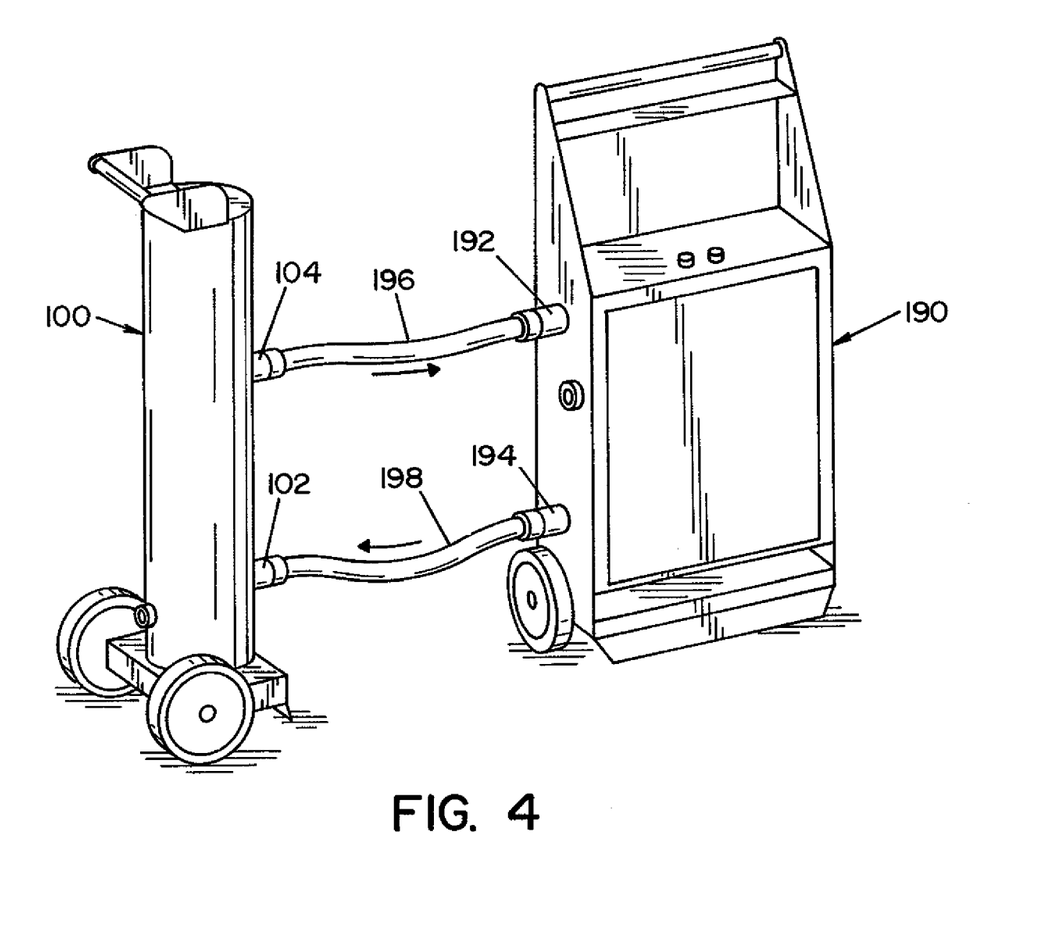
FIG. 4 is a perspective view of a dryer of a modular VHP decontamination system attached to a dryer regenerator for regeneration of the dryer.

It should be appreciated that the use of detachable dryer 100 allows dryers of different capacities to be connected with VHP unit 20, wherein the size of dryer 100 can be selected depending upon the volume of enclosure 4. It should be further appreciated that by providing dryer 100 as a separate tank detachable from VHP unit 20, dryer 100 can be conveniently "regenerated" using a dryer regenerator unit 190 (see FIG. 4). In this regard, dryer 100 can be detached from VHP unit 20 and attached to regenerator unit 190, while a substitute dryer is connected with VHP unit 20 during the regeneration process. Therefore, one or more decontamination cycles can be completed with the substitute dryer, while dryer 100 is being regenerated. FIG. 4 illustrates dryer 100 connected with regenerator unit 190. Regenerator unit 190 includes an inlet port 192 and an outlet port 194. A first conduit 196 is connected between outlet port 104 of dryer 100 and inlet port 192 of regenerator unit 190. Similarly, a second conduit 198 is connected between inlet port 102 of dryer 100 and outlet port 194 of regenerator unit 190. Regenerator unit 190 removes moisture collected by the desiccant medium (e.g., silica gel, activated alumina and molecular sieve) of dryer 100 by conventional means. In this regard, regenerator unit 190 may use purge air, heat or a combination of both, and thereby regenerate the dryer.

In a preferred embodiment of the present invention, dryer 100 is also adapted to receive a removable insulating jacket (not shown). An insulating jacket surrounds the outer housing of dryer 100 during the regeneration process to retain heat within dryer 100, thereby facilitating the regeneration process. The insulating jacket is preferably removed when dryer 100 is used in a decontamination cycle. Removal of the insulating jacket allows dryer 100 to remain cool during the decontamination cycle, thereby facilitating the removal of moisture by the desiccant.

External blower unit 150 is detachable from VHP unit 20, and includes a blower 152, driven by a motor 154. Motor 154 is controlled by control signals transmitted by controller 22 via a data cable 26. External blower unit 150 also includes an inlet conduit 156 having an inlet port 157, an outlet conduit 158 having an outlet port 159, and a receiver conduit 162 having an input port 163. Receiver conduit 162 is fluidly connected at a first end with supply conduit 32 of VHP unit 20, via a blower conduit 172. In this regard, blower conduit 172 is fluidly connected with output port 35 of supply conduit 32 and input port 163 of external blower unit 150. A second end of receiver conduit 162 is fluidly connected with outlet conduit 158. Fluid from region 6 is drawn into external blower unit 150 through inlet port 157 of inlet conduit 156. Fluid from supply conduit 32 of VHP unit 20 is received into receiver conduit 162. Fluid exits external blower unit 150 through outlet port 159 of outlet conduit 158. External blower unit 150 may also include a temperature sensor 166 that provides a signal indicative of the fluid temperature inside receiver conduit 162. Controller 22 receives the signal provided by temperature sensor 166. The temperature indicated by temperature sensor 166 is used in determining the maximum injection rate attainable before condensation occurs in receiver conduit 162, as will be discussed below. In an embodiment of the present invention wherein external blower is not used, temperature sensor 166 is located in a conduit downstream of vaporizer 56. External blower unit 150 is connected to a power source via a power cord 151. In the illustrated embodiment, power cord 151 is connected to an electrical outlet provided in VHP unit 20.

Contactor unit 140 is an external power switching means for controlling power to one or more components of system 16. In this regard, contactor unit 140 is comprised of one or more electrical outlets 142 that are connected with a power source via a power cord 141 (see FIG. 1). In the illustrated embodiment, power cord 141 is connected to a room electrical outlet 8. Power to each electrical outlet 142 is controlled by operation of a respective relay switch (not shown). Each relay switch is moveable between an open position and a closed position, wherein the respective electrical outlet 142 is connected to the power source when the relay switch is in the closed position, and the respective electrical outlet 142 is disconnected from the power source when the relay switch is in the open position. A data cable 26 connects contactor unit 140 with controller 22 of VHP unit 20. Controller 22 transmits control signals to contactor unit 140 via data cable 26 to control the state of each relay switch. Accordingly, control signals from controller 22 are used to control the state of each electrical outlet 142.

External destroyer 120 includes an inlet 122 and an outlet 124. External destroyer 120 is preferably a catalytic destroyer operable to destroy vaporized hydrogen peroxide flowing therethrough, by converting vaporized hydrogen peroxide into water and oxygen, as is conventionally known. Controller 22 communicates with external destroyer 120 via a data cable 26. External destroyer 120 is connected to a power source via a power cord 121 (see FIG. 1). In the illustrated embodiment, power cord 121 is connected to a room electrical outlet 8. Alternatively, power cord 121 may be connected with an electrical outlet 142 of contactor unit 140. Therefore, in the alternative embodiment, power is provided to external destroyer 120 in accordance with the state of a relay switch of contactor unit 140 that is controlled by controller 22.

External dryer 130 includes an inlet 132 and an outlet 134. External dryer 130 is preferably a conventionally known refrigerative dehumidifier that collects water vapor from the fluid stream passing therethrough. It should be understood that dryer 90 may take other forms including a desiccant dryer. In the illustrated embodiment, external dryer 130 includes a power cord 131 that is connected with an electrical outlet 142 of contactor unit 140. Therefore, power is provided to external dryer 130 in accordance with the state of a relay switch of contactor unit 140 that is controlled by controller 22.

Sensor module 110 is located within region 6, and may include, but is not limited to, a vaporized hydrogen peroxide ($H_2O_2$) concentration sensor for sensing the concentration of vaporized $H_2O_2$, a humidity sensor for determining the amount of moisture (relative humidity), and a temperature sensor for providing a signal indicative of the temperature in region 6. The sensors of sensor module 110 provide signals to controller 22, via data cable 26. It is contemplated that sensor module 110 may be alternatively located within VHP unit 20.

As illustrated in FIG. 1, VHP unit 20, dryer 100, external blower unit 150, external destroyer 120, external dryer 130 and contactor unit 140 are individual components that are interconnected to form system 16. VHP unit 20, dryer 100, external blower unit 150, and external dryer 130 preferably include housings that are supported by wheels to facilitate transportation and placement thereof. External destroyer 120 may also be configured with a housing supported by wheels. It should be appreciated that the various components of system 16 can be powered through different electrical circuits by connecting the respective power cords of each component to room electrical outlets 8 that are on different circuits. Accordingly, an overload condition can be avoided.

The present invention shall now be further described with reference to the operation of VHP decontamination system 16. Room 4, VHP unit 20 and external blower unit 150 define a closed loop fluid circulation path. In this regard, blower 66 draws fluid from region 6 into return conduit 34. As the fluid passes through return conduit 34, catalytic destroyer 64 breaks down the vaporized hydrogen peroxide in the fluid into water and oxygen. The fluid travels from return conduit 34 to dryer 100. As the fluid passes through dryer 100, water vapor is removed. After passing through dryer 100, the fluid travels through supply conduit 32. As the fluid passes through supply conduit 32, preheater 54 heats the fluid to facilitate the vaporization process of vaporizer 56. Vaporizer 56 includes a heated surface to vaporize the aqueous solution of hydrogen peroxide supplied thereto from reservoir 84. As indicated above, pump 96 supplies a metered amount of the hydrogen peroxide solution to vaporizer 56. Vaporized hydrogen peroxide exits supply conduit 32 and enters external blower unit 150 via blower conduit 172 and receiver conduit 162. Blower 152 disperses the vaporized hydrogen peroxide into region 6, thereby completing the closed loop fluid circulation path.

VHP decontamination system 16 has four (4) basic operating phases, namely, a dehumidification phase, a conditioning phase, a decontamination phase, and an aeration phase. In the dehumidification phase, the humidity within region 6 of room 4 is reduced by using dryer 100 to remove water vapor therefrom. Controller 22 may also activate external dryer 130 during the dehumidification phase to facilitate the removal of moisture from region 6. In the illustrated embodiment, controller 22 activates external dryer 130 via control signals transmitted to contactor unit 140. Fluid within region 6 is drawn into external dryer 130 via inlet 132. Fluid exits external dryer 130 via outlet 134. After the dehumidification phase is completed, the conditioning phase commences, wherein the aqueous solution of hydrogen peroxide is vaporized by vaporizer 56 and injected into region 6 at a relatively high rate by external blower unit 150, thereby rapidly increasing the concentration of vaporized hydrogen peroxide inside region 6. Following the conditioning phase, the decontamination phase commences wherein the decontaminant injection rate is regulated to maintain the vaporized hydrogen peroxide concentration inside region 6 at a desired constant concentration level. In the aeration phase that follows the decontamination phase, room 4 is aerated by stopping injection of the vaporized hydrogen peroxide into region 6, and removing vaporized hydrogen peroxide therefrom. In this regard, catalytic destroyer 64 of VHP unit 20 breaks down the vaporized hydrogen peroxide into water and oxygen. Controller 22 may also activate external destroyer 120 during the aeration phase to facilitate the aeration process. Fluid within region 6 is drawn into external destroyer 120 via inlet 122. Fluid exits external destroyer 120 via outlet 124. Aeration continues until the vaporized hydrogen peroxide concentration level in region 6 is below an acceptable threshold concentration level (e.g., 1 ppm). It should be noted that external dryer 130 is typically not activated during the conditioning and decontamination phases of the decontamination cycle.

Throughout the respective operating phases, the humidity sensor, temperature sensor, and vaporized hydrogen peroxide ($H_2O_2$) concentration sensor of sensor module 110 respectively monitor the relative humidity (RH), temperature, and vaporized hydrogen peroxide concentration within region 6, and provide electrical signals to controller 22 indicative of the relative humidity, temperature, and vaporized hydrogen peroxide concentration. Controller 22 determines the absolute humidity (AH) from the relative humidity (RH), as is conventionally known.

In accordance with one embodiment of the present invention, controller 22 is programmable to provide "feedback control." Feedback control automatically adjusts the injection rate of the aqueous hydrogen peroxide to insure that the vaporized hydrogen peroxide concentration inside region 6 does not reach a saturation concentration, and thus produce condensation within region 6. In this regard, at least one vaporized hydrogen peroxide concentration level and one "D value" are programmed into controller 22. In the illustrated embodiment, two (2) vaporized hydrogen peroxide ($H_2O_2$) concentration levels (a low concentration level (e.g., 250 ppm) and a high concentration level (e.g., 400 ppm)) are programmed into controller 22. In accordance with the programmed "D value," controller 22 determines a required exposure time for each programmed vaporized $H_2O_2$ concentration level, in a conventionally known manner. The exposure time is the minimum required time for exposure to the decontaminant (i.e., hydrogen peroxide) in order to effect decontamination.

Controller 22 is also programmed with a dew point margin ($\Delta_{MARGIN}$). The dew point margin ($\Delta_{MARGIN}$) is a delta value that is indicative of the minimum acceptable difference between: (1) the actual vaporized $H_2O_2$ concentration (as sensed by vaporized $H_2O_2$ concentration sensor and (2) the dew point concentration for the hydrogen peroxide vapor ($C_{DP}$), as calculated by controller 22. As will be explained below, the dew point margin ($\Delta_{MARGIN}$) is used to prevent the actual vaporized $H_2O_2$ concentration ($C_{ACTUAL}$) from exceeding the dew point concentration for the vaporized hydrogen peroxide vapor ($C_{DP}$). As a result, condensation of vaporized hydrogen peroxide inside region 6 is prevented.

During the conditioning and decontamination phases of the decontamination cycle, controller 22 will operate system 16 to prevent condensation of vaporized hydrogen peroxide within region 6. In this regard, controller 22 uses data provided by the humidity sensor, together with data provided by the temperature probe, to calculate the absolute water vapor concentration within region 6. Using the calculated absolute water vapor concentration, controller 22 determines the dew point concentration for the hydrogen peroxide vapor ($C_{DP}$) at the temperature inside region 6. Controller 22 also monitors the actual vaporized $H_2O_2$ concentration ($C_{ACTUAL}$) inside region 6 using the vaporized $H_2O_2$ concentration sensor.

Controller 22 determines a measured delta value ($\Delta_{MEASURED}$) that is the difference between: (1) the actual vaporized $H_2O_2$ concentration ($C_{ACTUAL}$) inside region 6 and (2) the dew point concentration for the hydrogen peroxide vapor ($C_{DP}$). If the measured delta value ($\Delta_{MEASURED}$) is less than the dew point margin ($\Delta_{MARGIN}$), then the actual vaporized $H_2O_2$ concentration ($C_{ACTUAL}$) is approaching the dew point concentration for the hydrogen peroxide vapor ($C_{DP}$). Accordingly, controller 22 will take appropriate action to increase the measured delta value ($\Delta_{MEASURED}$) to a value greater than the dew point margin ($\Delta_{MARGIN}$). In the illustrated embodiment, controller 22 increases the measured delta value ($\Delta_{MEASURED}$) to a value greater than the dew point margin ($\Delta_{MARGIN}$) by decreasing the injection rate of the aqueous solution of hydrogen peroxide to vaporizer 56, thereby reducing the actual vaporized $H_2O_2$ concentration ($C_{ACTUAL}$) inside chamber or region 6.

Controller 22 may also be programmed to operate first and second timers for determining exposure time during operation of system 16. The first timer is used to monitor the actual exposure time for a programmed low $H_2O_2$ concentration level (e.g., 250 ppm) and the second timer is used to monitor the actual exposure time for a programmed high $H_2O_2$ concentration level (e.g., 400 ppm). Accordingly, the first timer is started when the actual $H_2O_2$ concentration ($C_{ACTUAL}$) has reached the programmed low $H_2O_2$ concentration level, and continues timing as long as the actual $H_2O_2$ concentration ($C_{ACTUAL}$) remains at, or above, the programmed low $H_2O_2$ concentration level. The second timer is started when the actual $H_2O_2$ concentration ($C_{ACTUAL}$) has reached the programmed high $H_2O_2$ concentration level, and continues timing as long as the actual $H_2O_2$ concentration ($C_{ACTUAL}$) remains at, or above, the programmed high $H_2O_2$ concentration level.

A decontamination cycle is determined to have been successfully completed when the $H_2O_2$ concentration level has been maintained within region 6 for the exposure time corresponding to the $H_2O_2$ concentration level. As discussed above, the exposure time for a given $H_2O_2$ concentration level is determined by controller 22 in accordance with a programmed "D value." If controller 22 has been programmed to operate system 16 at the high $H_2O_2$ concentration level, but system 16 is unable to achieve the high $H_2O_2$ concentration level, then controller 22 will automatically switch to operating system 16 at the low $H_2O_2$ concentration level. The high $H_2O_2$ concentration level may not be achievable because the maximum injection rate is insufficient to obtain the high $H_2O_2$ concentration level, or controller 22 may determine that the measured delta value ($\Delta_{MEASURED}$) is less than the dew point margin ($\Delta_{MARGIN}$), thereby indicating that the actual $H_2O_2$ concentration ($C_{ACTUAL}$) has approached the dew point concentration for the hydrogen peroxide vapor ($C_{DP}$).

In some cases, the high $H_2O_2$ concentration level may be achievable, but the time required to reach the high $H_2O_2$ concentration level may be relatively long. Accordingly, controller 22 determines whether it is faster to modify the operation of system 16 to operate at the low $H_2O_2$ concentration level. In this respect, controller 22 compares the remaining time needed to complete a successful decontamination cycle at the low $H_2O_2$ concentration level (taking into consideration the current value of the first timer) with the estimated time needed to complete a successful decontamination cycle at the high $H_2O_2$ concentration level (taking into consideration the rate at which the $H_2O_2$ concentration level is increasing per unit time). The rate at which the $H_2O_2$ concentration level is increasing per unit time can be determined from the slope of the $H_2O_2$ concentration level versus time curve. If controller 22 determines that a successful decontamination cycle can be completed sooner at the low $H_2O_2$ concentration level, then controller 22 will reduce the $H_2O_2$ concentration level in region 6 to the programmed low $H_2O_2$ concentration level for the remaining duration of the decontamination cycle.

During the conditioning phase it is desirable to rapidly inject vaporized hydrogen peroxide into region 6 without condensing the vaporized hydrogen peroxide in any conduits or at the outlet of vaporizer 56. Therefore, controller 22 preferably uses the temperature as indicated by temperature sensor 166 of external blower unit 150 when determining the dew point concentration during the conditioning phase.

Controller 22 may also be programmed to provide "cycle replay." Cycle replay allows controller 22 to repeat control operations that have been used for a previous decontamination cycle. In this regard, system 16 may be conveniently used to decontaminate multiple enclosures (e.g., laboratory rooms) having substantially the same properties, i.e., substantially the same volume, and substantially the same room temperature. The multiple enclosures may even contain similar articles (e.g., workbenches). With cycle replay, controller 22 is programmable to store operating parameters (e.g., decontaminant injection rates obtained using feedback control, as described above) developed during a previous decontamination cycle, and to re-use the stored operating parameters to "replay" the decontamination cycle. Accordingly, a decontamination cycle can be repeated for the same enclosure at a later time, or the decontamination cycle can be repeated in other enclosures having substantially the same properties.

As indicated above, controller 22 may activate external dryer 130 by transmitting control signals to contactor unit 140 that energizes (i.e., closes) the relay switch associated with external dryer 130. In this manner, the time required to complete the dehumidification phase can be reduced by the simultaneous operation of dryer 100 and external dryer 130. The extra dehumidification capacity provided by external dryer 130 is particularly desirable where enclosure 4 has a large volume (e.g., laboratory room).

During the aeration phase of the decontamination cycle, it is desirable to rapidly remove vaporized hydrogen peroxide from region 6. Therefore, controller 22 preferably activates external destroyer 120 during the aeration phase to more quickly break down the vaporized hydrogen peroxide into water and oxygen. As a result, the time to complete the aeration phase can be reduced by the simultaneous operation of destroyer 64 of VHP unit 20 and external destroyer 120. The extra aeration capacity provided by external destroyer 120 is particularly desirable where region 6 has a large volume (e.g., laboratory rooms).

Figure 3:
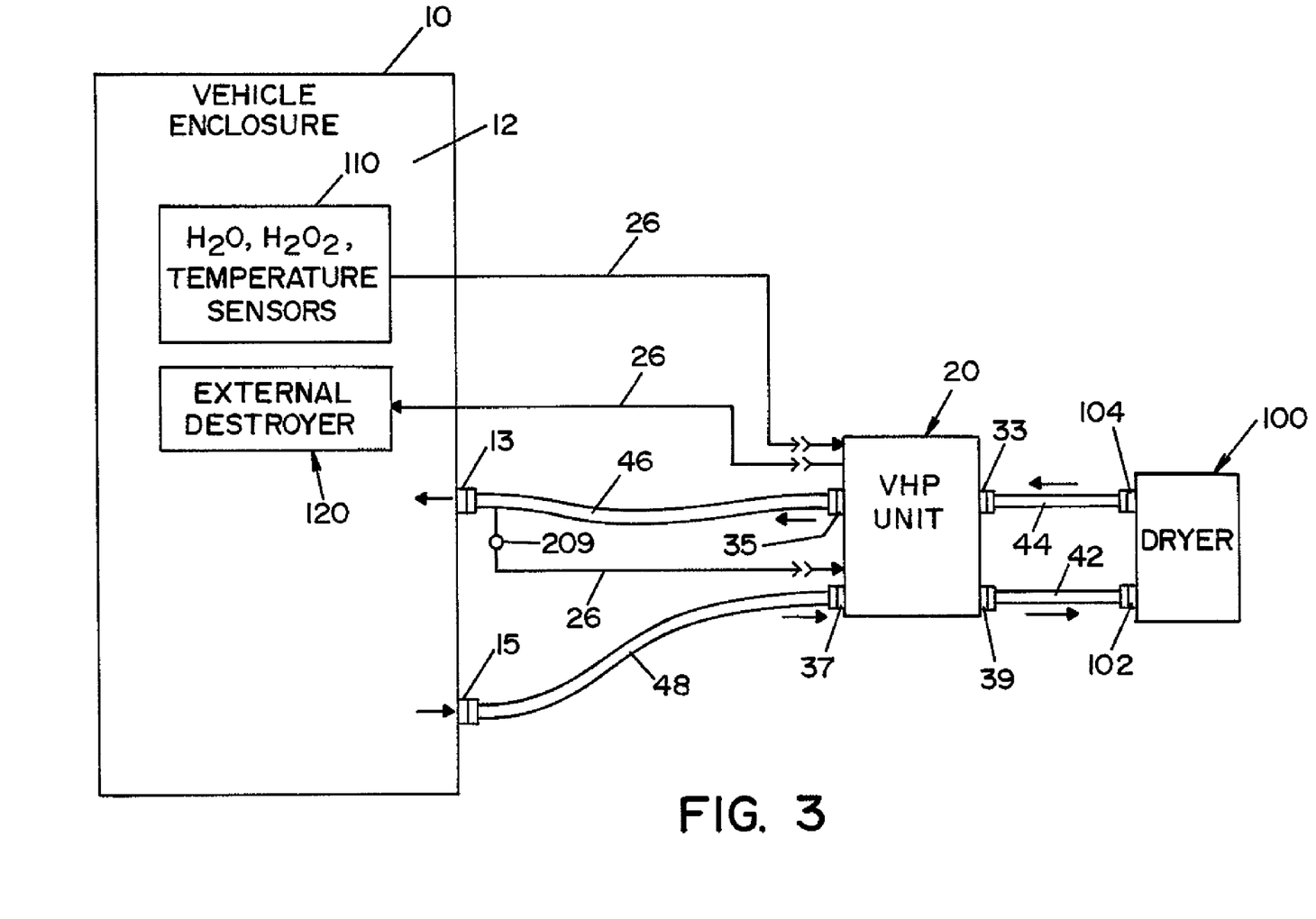
FIG. 3 is a schematic view of a modular VHP decontamination system according to an alternative embodiment of the present invention.

FIG. 3 illustrates an alternative embodiment of the present invention. In this embodiment, the enclosure takes the form of a patient compartment 10 of an emergency vehicle (e.g., an ambulance or an emergency rescue vehicle). Patient compartment 10 defines a chamber or region 12. Patient compartment 10 includes an input port 13 and an output port 15. In this embodiment of the present invention, VHP unit 20 and dryer 100 are located outside region 12. Output port 35 and input port 37 of VHP unit 20 are fluidly connected with region 12 via entry conduit 46 and exit conduit 48. In this regard, entry conduit 46 is extends between output port 35 of VHP unit 20 and input port 13 of patient compartment 10, while exit conduit 48 extends between input port 37 of VHP unit 20 and output port 15 of patient compartment 10. A temperature sensor 209 is located within entry conduit 46 to provide a signal indicative of the temperature therein. Temperature sensor 209 serves the same function as temperature sensor 166 of the first embodiment described above. Sensor module 110 and external destroyer 120 are located within region 12. Data cables 26 connect sensors 110 and external destroyer 120 with controller 22 of VHP unit 20. In the illustrated embodiment, blower 66 of VHP unit 20 is used to disperse the vaporized hydrogen peroxide in region 12. It should be appreciated that an external dryer 130 and an external blower unit 150 may also be located within region 12.

As discussed above, controller 22 may be connected with flash memory device 29 and USB memory device 28. Flash memory device 29 may be used to store program code for operation of controller 22, as well as decontamination cycle data and sensor calibration data for the sensors of sensor module 110. If the program code for controller 22 needs to be changed, the original flash memory device 29 can be removed and replaced with a new flash memory device 29 storing a different program code. In order to avoid the need to manually reload decontamination cycle data and sensor calibration data that had been stored on the original flash memory device 29, the decontamination cycle data and the sensor calibration data are copied from the original flash memory device 29 to USB memory device 28, before removal of the original flash memory device 29. Once the new flash memory device 29 is installed, decontamination cycle data and sensor calibration data are copied from USB memory device 28 to the new flash memory device 29.

The USB memory device 28 can also be used to data log decontamination cycle data, including but not limited to, $H_2O_2$ concentration, sensor data and other parameters affecting decontamination cycle performance. Data stored to USB memory device 29 is preferably encrypted for security. Accordingly, USB memory device 28 also stores a program to decrypt the stored data. An encrypted decontamination cycle record that can be printed using printer 24 may also be stored to USB memory device 28.

Sensor calibration data for each sensor of sensor module 110 may be stored on a USB memory device that is located within the respective sensor. Each sensor comprising sensor module 110 is preferably daisy-chained together. At the beginning of each decontamination cycle controller 22 prompts the user to input a serial number for each sensor of sensor module 110 that is connected to VHP unit 20. If the calibration data for each sensor is not stored in controller 22, the user is prompted to take the USB memory device from the sensor and insert it into the USB port connected directly to controller 22. The calibration data is then loaded into controller 22. As long as the same sensors are connected in a given order, the calibration data stored in controller 22 can be used for future decontamination cycles.

In an embodiment of the present invention, controller 22 includes an Ethernet network adapter. Controller 22 preferably supports a public domain program known as "VNC viewer" that allows a conventional personal computer connected to the Ethernet port to operate controller 22 using mouse clicks to actuate keys on the touch screen or panel of controller 22. If a wireless router is connected to the Ethernet port and a personal computer has a wireless Ethernet adapter, then controller 22 can be operated wirelessly from a remote location using the personal computer. Wireless communication with controller 22 can also be used to read wireless $H_2O_2$ concentration sensors. Wireless control allows system 16 to be operated from a location remote from a room being decontaminated.

System 16 may also include an $H_2O_2$ alarm sensor that is mounted outside the enclosure being decontaminated to detect leakage of $H_2O_2$ outside the enclosure during a decontamination cycle. A signal generated by a remotely mounted external $H_2O_2$ alarm sensor can be used to automatically abort a decontamination cycle. In this regard, the $H_2O_2$ alarm sensor is electrically connected with controller 22 to transmit alarm signals thereto.

The foregoing description is a specific embodiment of the present invention. It should be appreciated that this embodiment is described for purposes of illustration only, and that numerous alterations and modifications may be practiced by those skilled in the art without departing from the spirit and scope of the invention. For example, in the illustrated embodiment of the present invention, the liquid decontaminant is an aqueous solution of hydrogen peroxide. It is contemplated that the present invention may find advantageous application with decontamination systems using other vapor-phase decontaminants. Furthermore, it is also contemplated that the present invention may be configured to permit condensation of vaporized hydrogen peroxide vapor at very low levels (i.e., "micro-condensation") in order to provide a layer of hydrogen peroxide condensate directly to the surfaces to be treated. It is intended that all such modifications and alterations be included insofar as they come within the scope of the invention as claimed or the equivalents thereof.

Having described the invention, the following is claimed:

1. A vapor decontamination system for decontaminating a region, said system comprising:
    (a) a main unit including:
        a reservoir for providing an aqueous solution of hydrogen peroxide,
        a vaporizer for generating vaporized hydrogen peroxide from the aqueous solution of hydrogen peroxide,
        at least one humidity sensor providing a first signal indicative of moisture in the region,
        a temperature sensor providing a second signal indicative of the temperature in the region,
        at least one concentration sensor providing a third signal indicative of the concentration of the decontaminant in the region,
        a first destroyer for breaking down said vaporized hydrogen peroxide,
        a first input port,
        first and second output ports,
        a controller for controlling operation of the vapor decontamination system,
        input means for inputting into the controller one of: (a) a first concentration level and a first exposure time associated therewith, or (b) a first concentration level and a D-value indicative of a desired reduction of bioburden, wherein a first exposure time associated with the first concentration level is determined according to the D-value,
        said controller communicating with said vaporizer to control the rate at which vaporized hydrogen peroxide is injected into the region, and receiving the first, second, and third signal, wherein said controller is programmed to:
            inject the vaporized hydrogen peroxide into the region at an injection rate for obtaining the first concentration level of vaporized decontaminant in the region,
            monitor actual concentration of the vaporized hydrogen peroxide in the region,
            determine dew point concentration of the vaporized hydrogen peroxide in the region,
            determine whether the actual concentration of the vaporized hydrogen peroxide in the region is at least a predetermined amount below the dew point concentration of the vaporized hydrogen peroxide in the region, and
            decrease the actual concentration of the vaporized hydrogen peroxide if the actual concentration of the vaporized hydrogen peroxide in the region is not at least the predetermined amount below the dew point concentration of the vaporized hydrogen peroxide in the region;

(b) a first dryer detachable from said main unit, said first dryer including:
an inlet port fluidly connectable with said first output port, and
an outlet port fluidly connectable with said first input port; and (c) a mobile blower unit detachable from the main unit, the blower unit fluidly connectable with the second output port of the main unit, and controlled by the controller of the main unit.

2. A vapor decontamination system as defined in claim 1, wherein said system further comprises:
external power switching means having a plurality of switchable electrical outlets controllable by said controller.

3. A vapor decontamination system as defined in claim 2, wherein at least one of a second destroyer and a second dryer are electrically connected to the external power switching means for supplying power thereto.

4. A vapor decontamination system as defined in claim 1, wherein said controller records operating parameters associated with control of the vapor decontamination system during a first decontamination cycle and repeats the operating parameters for a subsequent decontamination cycle.

5. A vapor decontamination system as defined in claim 1, wherein said system further comprises a dryer regeneration unit, said dryer regeneration unit fluidly connectable with said first dryer.

6. A vapor decontamination system according to claim 1, wherein said vapor decontamination system further comprises:
a second dryer external to said main unit, said second dryer activated by said controller of said main unit;
wherein said main unit, said first dryer, said blower unit, and said second dryer each include a housing supported by wheels to facilitate transportation thereof.

7. A vapor decontamination system according to claim 1, wherein said main unit includes a leak detection means for detecting the presence of the aqueous solution of hydrogen peroxide in a collecting region of said main unit.

8. A vapor decontamination system according to claim 7, wherein said leak detection means includes at least one of the following: a float switch or a conductivity sensor.

9. A vapor decontamination system according to claim 1, wherein said first dryer includes a removable insulating blanket.

10. A vapor decontamination system according to claim 1, wherein said system further comprises:
a first removable memory device for storing sensor calibration data; and
a second removable memory device for storing a copy of the sensor calibration data stored in said first removable memory device.

11. A vapor decontamination system according to claim 10, wherein said second removable memory device stores encrypted data associated with a decontamination cycle.

12. A vapor decontamination system according to claim 10, wherein said first removable memory device is a flash memory device.

13. A vapor decontamination system according to claim 10, wherein said second removable memory device is a USB memory device.

14. A vapor decontamination system according to claim 1, wherein said controller includes a network adapter for remote operation of said controller via a wired or wireless network.

15. A vapor decontamination system according to claim 1, wherein said system further comprises:
an $H_2O_2$ alarm sensor for detecting leakage of $H_2O_2$ outside said region during a decontamination cycle.

16. A vapor decontamination system according to claim 1, wherein said controller is further programmed to:
initiate a first timer when the actual concentration of the vaporized decontaminant in the region reaches the first concentration level, wherein the first timer indicates the total time that the actual concentration of the vaporized decontaminant in the region is at or above the first concentration level; and
initiate a second timer when the actual concentration of the vaporized decontaminant in the region reaches a second concentration level, wherein a second exposure time is associated with the second concentration level, the second timer indicating the total time that the actual concentration of the vaporized decontaminant in the region is at or above the second concentration level;
determine a first time value indicative of the amount of time needed to complete a successful decontamination cycle at the first concentration level;
determine a second time value indicative of the amount of time needed to complete a successful decontamination cycle at the second concentration level; and
inject vaporized decontaminant into the region at an injection rate for obtaining one of said first and second concentration levels based upon a comparison of the first and second time values.

17. A vapor decontamination system for decontaminating a region, said system comprising:
(a) a main unit including:
a reservoir for providing an aqueous solution of hydrogen peroxide,
a vaporizer for generating vaporized hydrogen peroxide from the aqueous solution of hydrogen peroxide,
at least one humidity sensor providing a first signal indicative of moisture in the region,
a temperature sensor providing a second signal indicative of the temperature in the region,
at least one concentration sensor providing a third signal indicative of the concentration of the decontaminant in the region,
a first destroyer for breaking down said vaporized hydrogen peroxide,
a first input port,
first and second output ports,
a controller for controlling operation of the vapor decontamination system,
input means for inputting into the controller one of: (a) a first concentration level and a first exposure time associated therewith, or (b) a first concentration level and a D-value indicative of a desired reduction of bioburden, wherein a first exposure time associated with the first concentration level is determined according to the D-value,
said controller communicating with said vaporizer to control the rate at which vaporized hydrogen peroxide is injected into the region, and receiving the first, second, and third signal, wherein said controller is programmed to:
inject the vaporized hydrogen peroxide into the region at an injection rate for obtaining the first concentration level of vaporized decontaminant in the region,
monitor the actual concentration of the vaporized hydrogen peroxide in the region, determine the dew point concentration of the vaporized hydrogen peroxide in the region,
determine whether the actual concentration of the vaporized hydrogen peroxide in the region is at least a predetermined amount below the dew point concentration of the vaporized hydrogen peroxide in the region, and
decrease the actual concentration of the vaporized hydrogen peroxide if the actual concentration of the vaporized hydrogen peroxide in the region is not at least the predetermined amount below the dew point concentration of the vaporized hydrogen peroxide in the region;
(b) a first dryer detachable from said main unit, said first dryer including:
an inlet port fluidly connectable with said first output port, and
an outlet port fluidly connectable with said first input port; and
(c) a mobile second destroyer external to the main unit, said second destroyer activated by the controller of the main unit.

18. A vapor decontamination system according to claim 17, wherein said controller is further programmed to:
initiate a first timer when the actual concentration of the vaporized decontaminant in the region reaches the first concentration level, wherein the first timer indicates the total time that the actual concentration of the vaporized decontaminant in the region is at or above the first concentration level; and
initiate a second timer when the actual concentration of the vaporized decontaminant in the region reaches a second concentration level, wherein a second exposure time is associated with the second concentration level, the second timer indicating the total time that the actual concentration of the vaporized decontaminant in the region is at or above the second concentration level;
determine a first time value indicative of the amount of time needed to complete a successful decontamination cycle at the first concentration level;
determine a second time value indicative of the amount of time needed to complete a successful decontamination cycle at the second concentration level; and
inject vaporized decontaminant into the region at an injection rate for obtaining one of said first and second concentration levels based upon a comparison of the first and second time values.

19. A vapor decontamination system for decontaminating a region, said system comprising:
(a) a main unit including:
a reservoir for providing an aqueous solution of hydrogen peroxide,
a vaporizer for generating vaporized hydrogen peroxide from the aqueous solution of hydrogen peroxide,
at least one humidity sensor providing a first signal indicative of moisture in the region,
a temperature sensor providing a second signal indicative of the temperature in the region,
at least one concentration sensor providing a third signal indicative of the concentration of the decontaminant in the region,
a first destroyer for breaking down said vaporized hydrogen peroxide,
a first input port,
first and second output ports,
a controller for controlling operation of the vapor decontamination system,
input means for inputting into the controller one of: (a) a first concentration level and a first exposure time associated therewith, or (b) a first concentration level and a D-value indicative of a desired reduction of bioburden, wherein a first exposure time associated with the first concentration level is determined according to the D-value,
said controller communicating with said vaporizer to control the rate at which vaporized hydrogen peroxide is injected into the region, and receiving the first, second, and third signal, wherein said controller is programmed to:
inject the vaporized hydrogen peroxide into the region at an injection rate for obtaining the first concentration level of vaporized decontaminant in the region,
monitor the actual concentration of the vaporized hydrogen peroxide in the region,
determine the dew point concentration of the vaporized hydrogen peroxide in the region,
determine whether the actual concentration of the vaporized hydrogen peroxide in the region is at least a predetermined amount below the dew point concentration of the vaporized hydrogen peroxide in the region, and
decrease the actual concentration of the vaporized hydrogen peroxide if the actual concentration of the vaporized hydrogen peroxide in the region is not at least the predetermined amount below the dew point concentration of the vaporized hydrogen peroxide in the region;
(b) a first dryer detachable from said main unit, said first dryer including:
an inlet port fluidly connectable with said first output port, and
an outlet port fluidly connectable with said first input port; and
(c) a mobile second dryer external to the main unit, said second dryer activated by the controller of the main unit.

20. A vapor decontamination system according to claim 19, wherein said controller is further programmed to:
initiate a first timer when the actual concentration of the vaporized decontaminant in the region reaches the first concentration level, wherein the first timer indicates the total time that the actual concentration of the vaporized decontaminant in the region is at or above the first concentration level; and
initiate a second timer when the actual concentration of the vaporized decontaminant in the region reaches a second concentration level, wherein a second exposure time is associated with the second concentration level, the second timer indicating the total time that the actual concentration of the vaporized decontaminant in the region is at or above the second concentration level;
determine a first time value indicative of the amount of time needed to complete a successful decontamination cycle at the first concentration level;
determine a second time value indicative of the amount of time needed to complete a successful decontamination cycle at the second concentration level; and
inject vaporized decontaminant into the region at an injection rate for obtaining one of said first and second concentration levels based upon a comparison of the first and second time values.

* * * * *